United States Patent [19]

Lang

[11] Patent Number: 4,715,918

[45] Date of Patent: Dec. 29, 1987

[54] METHOD FOR FORMING DISCRETE PARTICULATE AREAS IN A COMPOSITE ARTICLE

[75] Inventor: Theodore B. Lang, Appleton, Wis.

[73] Assignee: Kimberly-Clark Corporation, Neenah, Wis.

[21] Appl. No.: 749,158

[22] Filed: Jun. 26, 1985

[51] Int. Cl.$^4$ .................... B32B 31/06; B32B 31/08; B32B 31/12

[52] U.S. Cl. .................. 156/273.1; 156/276; 156/291; 156/292; 156/301; 156/324

[58] Field of Search ............... 156/276, 279, 291, 292, 156/62.2, 308.4, 301, 273.1

[56] References Cited

U.S. PATENT DOCUMENTS

| | | | |
|---|---|---|---|
| 2,695,244 | 11/1954 | Fountain | 156/279 |
| 3,296,965 | 1/1967 | Reif et al. | |
| 3,682,738 | 8/1972 | Smith | |
| 3,776,798 | 12/1973 | Milano | 156/291 |
| 3,888,257 | 6/1975 | Cook et al. | |
| 3,927,673 | 12/1975 | Taylor | |
| 4,055,180 | 10/1977 | Karami | 128/287 |
| 4,105,033 | 8/1978 | Chatterjee et al. | |
| 4,139,613 | 2/1979 | Hefele | |
| 4,260,443 | 4/1981 | Lindsay | |
| 4,284,465 | 8/1981 | Walbrun | |
| 4,296,234 | 10/1981 | Mindt et al. | |
| 4,297,410 | 10/1981 | Tsuchiya et al. | |
| 4,333,465 | 6/1982 | Wiegner | |
| 4,363,680 | 12/1982 | Buck et al. | |
| 4,381,783 | 5/1983 | Elias | |
| 4,437,294 | 3/1984 | Romagnoli | 53/555 |

FOREIGN PATENT DOCUMENTS

| | | | |
|---|---|---|---|
| 750479 | 1/1975 | South Africa | 128/287 |
| 2140471 | 11/1984 | United Kingdom | |

OTHER PUBLICATIONS

Rossman, "Now: A Plastic to Eat-Or Simply Dissolve in Water", *Package Engineering*, Jul. 1971, pp. 54–57.

Chemical Technology Review No. 78, "Specialty Papers", Gould-pp. 190–193.

Package Engineering, Jul. 1971-pp. 54–57, "Now: A Plastic to Eat-Or Simply Dissolve in Water"-J. M. Rossman.

*Primary Examiner*—Donald E. Czaja
*Assistant Examiner*—J. Davis
*Attorney, Agent, or Firm*—Paul A. Leipold; Donald L. Traut; Jeremiah J. Duggan

[57] ABSTRACT

The invention is generally accomplished by providing a roll having cavities suitable for retaining small quantities of particulate material. The roll further is adapted to be rotated such that the particulate material is deposited onto a web in discrete areas. These areas correspond to the depressions on the roll. The apparatus and method of the invention further provides in its preferred form a roll applicator device for adhesive having a series of lands and valleys wherein the lands correspond to the areas between the discrete particulate material. The applicator roll provides adhesive on the land areas that is transferred to a web of material which is brought into contact with the substrate bearing the discrete deposits of particulate material and sealed thereto. There is thereby provided areas of discrete particulate material securely separated by the adhesive connected webs.

In a preferred embodiment of the invention the particles are superabsorbent material and the composite web containing discrete areas of superabsorbent material is utilized in formation of an absorbent structure such as a diaper, incontinent garment or feminine pad.

14 Claims, 14 Drawing Figures

METHOD FOR FORMING DISCRETE PARTICULATE AREAS IN A COMPOSITE ARTICLE

TECHNICAL FIELD

This invention relates to improved methods and apparatus for forming composite articles having pockets of particulate material. It particularly relates to method and apparatus for forming improved absorbent articles having superabsorbent materials in discrete, separated areas.

BACKGROUND ART

It has been proposed in U.S. Pat. No. 4,381,783—Elias—to form an improved absorbent articles having several pockets of highly absorbent material.

U.S. Pat. No. 4,282,465—Walbrun—discloses a system for uniting two kinds of web material between embossed rolls. Further, it is disclosed that adhesive may be applied to one of the web materials as it rests on the lands of one of the embossed rolls.

U.S. Pat. No. 4,055,180—Karami—discloses an absorbent article that has pockets for retaining highly absorbent materials.

While it has been proposed that highly absorbent materials be placed in discrete locations on a substrate in order to better expose them to liquids without gel blocking or sagging, the placement and sealing of the particulate material into a large number of discrete areas has been unsatisfactory.

Methods using air forming of fibers and superabsorbent hydrocolloidal materials such as Great Britain Patent Application No. 2,140,471 are difficult to control and may cause lose of superabsorbent during forming as it is removed with the forming air. Further, air forming methods do not allow precise placement of superabsorbent materials in well-defined areas. There remains a need for a reliable, low-cost and effective method and apparatus for forming discrete areas of superabsorbent material.

DISCLOSURE OF THE INVENTION

It is an object of this invention to overcome disadvantages of prior art processes, apparatus and product.

It is an additional object of this invention to provide positive sealing of superabsorbent materials in discrete areas.

It is another object of this invention to provide a method of depositing multiple separate areas of particulate material between substrates.

It is a further object of this invention to provide an improved absorbent structure.

These and other objects of the invention are generally accomplished by providing a roll having cavities suitable for retaining small quantities of particulate material. The roll further is adapted to be rotated such that the particulate material is deposited onto a web in discrete areas. These areas correspond to the depressions on the roll. The apparatus and method of the invention further provides in its preferred form a roll applicator device for adhesive having a series of lands and valleys wherein the lands correspond to the areas between the discrete particulate material. The applicator roll provides adhesive on the land areas that is transferred to a web of material which is brought into contact with the substrate bearing the discrete deposits of particulate material and sealed thereto. There is thereby provided areas of discrete particulate material securely separated by the adhesive connected webs.

In a preferred embodiment of the invention the particles are superabsorbent material and the composite web containing discrete areas of superabsorbent material is utilized in formation of an absorbent structure such as a diaper, incontinent garment or feminine pad.

MODES FOR CARRYING OUT THE INVENTION

The invention has numerous advantages over the prior processes. The system of the invention allows uniform placement of the superabsorbent or other particulate material onto a substrate. It allows the accurate placement in zones that are controlled by the depth and spacing of the depressions on the applicator roll. The system has the advantage that superabsorbent will not fall out of the absorbent member when formed in accordance with the invention. The superabsorbent further will not shift or settle in the article during packing, shipping and wearing. Due to the increased efficiency of placement of the superabsorbent in particularly desired zones, it is possible to utilize less superabsorbent than other placement systems. The invention has the advantage that the superabsorbent or other particle is not released into the air as air-forming systems allow. As the superabsorbent is contained, it is not likely to be spilled or released onto the floor of the forming area, forming a slippery, unsafe surface. These and other advantages of the system will become apparent from the detailed description below.

Figure 1:
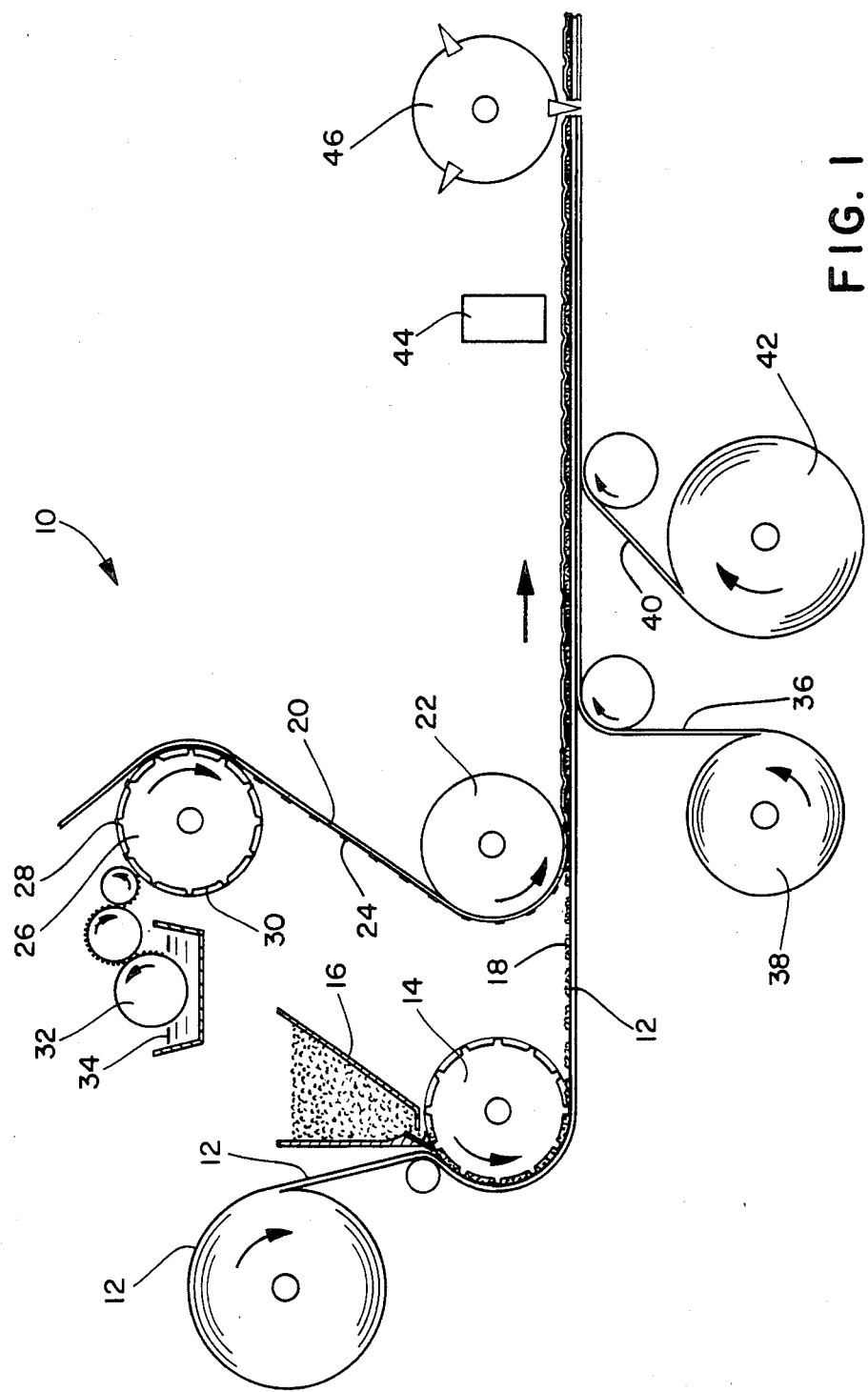
FIG. 1 is a schematic illustration of the apparatus for carrying out the invention.

Illustrated in FIG. 1 is a forming system 10 of the invention for an absorbent pad. The apparatus as shown schematically in FIG. 1 comprises a source of a receiving web material 12. The receiving web 12 may be a permeable member such as a spunbonded or permeable polypropylene web or a paper tissue. The receiving web 12 is conveyed, by means not shown, past the applicator roll for superabsorbent 18. Superabsorbent is supplied to applicator roll 14 from hopper source 16. The superabsorbent 18 is formed into discrete piles on the substrate 12 as the receiving web passes beneath the applicator roll 14. The receiving web 12 bearing the discrete piles 18 of superabsorbent passes beneath covering web 20 that is pressed into contact by bonding roll 22. The covering web 20 has applied thereto areas of adhesive 24. These areas of adhesive are applied by the adhesive applicator roll 26. The adhesive applicator roll 26 has a series of lands 28 and valleys 30. The lands 28 have adhesive applied thereto by rotating applicator roll 32 that is rotated in a source of adhesive 34. The covering web 20 may be any suitable material for the formation of absorbent garments and wraps and often would be an impermeable member such as a polypropylene or polyethylene film. The areas of adhesive 24 are placed in such a pattern that the areas of adhesive surround the discrete piles 18 of superabsorbent material and form isolated pockets. FIG. 1 illustrates the formation of an absorbent structure wherein the covering web 20 is impermeable, and the composite of the permeable member such as tissue 12 and polymer sheet 20 is further united with an absorbent member such as a batt of wood fluff 36 from source roll 38. Rather than wood fluff, a web of material such as coform which is an air-formed mixture of divellicated wood fibers and polypropylene meltblown material could also be utilized. After being united with a bulk absorbent member, the absorbent composite generally would have a permeable body-side member 40 from source roll 42 combined with the absorbent and superabsorbent carrying backing material. The permeable member may be wrapped around the composite to unite the garment at 44 and the composite cut at 46. The methods of formation of garments and absorbent members such as diapers, feminine products or adult incontinence garments is well-known. The system of the invention providing a controlled high absorbency composite is suitable for any of these products as well as other uses where absorbency is desirable.

Figure 2:
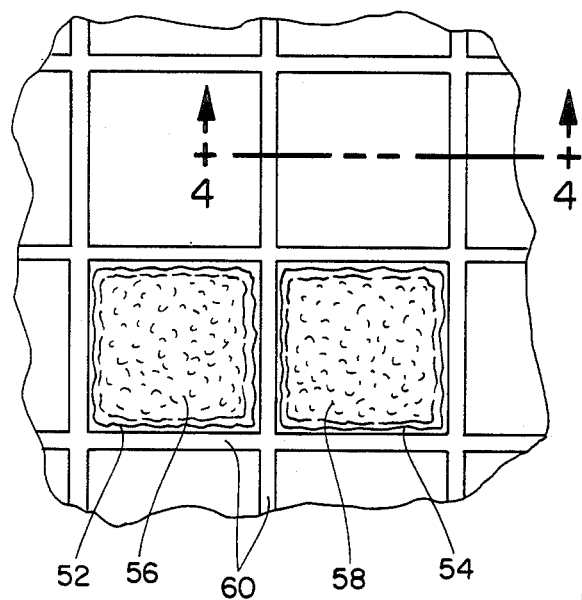
FIG. 2 is a view of a composite formed in accordance with the invention illustrating the areas where the webs are joined, separating discrete areas of particulate matter.

FIG. 2 is a cut-away view of a portion of a pad 50 formed in accordance with the invention. The pad has cut-away areas 52 and 54 where the piles of superabsorbent 56 and 58 are exposed. The areas of adhesive are illustrated by the cross-hatched pattern 60 that separates the piles of superabsorbent 56 and 58.

Figure 4:
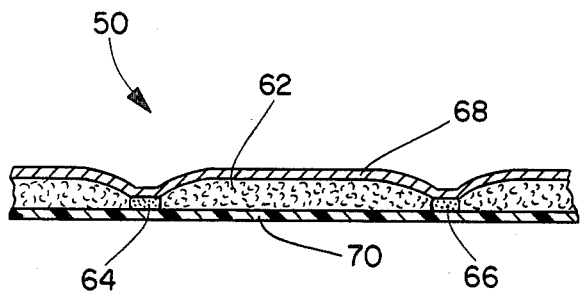
FIG. 4 is a cross section of FIG. 2 showing the formation of the discrete areas of particulate matter.

FIG. 4 is a cross section of FIG. 2 on line 4—4. As the view of FIG. 4 illustrates the individual piles such as 62 of superabsorbent are separated by the adhesive lines 64 and 66, that adhere the permeable cover 68 to the impermeable backing member 70.

Figure 3:
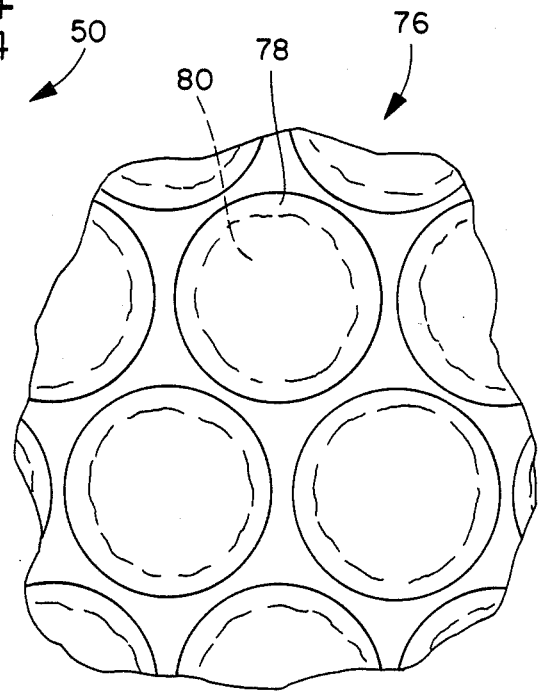
FIG. 3 is a view of a pad in accordance with the invention in which ring-shaped areas of adhesives are surrounding discrete areas of particulate material.

FIG. 3 illustrates a different pattern of superabsorbent and adhesive. The pad 76 is provided with generally circular areas 78 of adhesive that surround discrete areas of superabsorbent 80.

Figure 5:
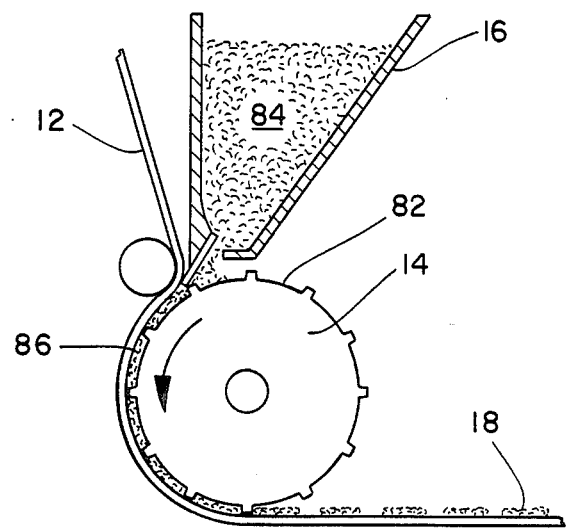
FIG. 5 is a fragmentary schematic of the applicator device.

FIG. 5 is enlarged schematic view of the applicator roll 14 and particulate dispenser or feeder 16. The dispenser roll 14 has a series of depressions 82 that pass underneath the feeder 16 where the particulate 84 passes to fill the depressions 82 with a deposit of the particulate matter 86. A receiving member 12 passes the roll and the particulate matter is deposited in separate discrete areas 18 onto the member.

The pattern of the roll may be any pattern desired that corresponds with the desired areas of particulate matter. In those instances where the particulate matter is a superabsorbent, the areas of superabsorbent concentration where absorbent properties are most needed may be controlled by controlling both the size of the depressions in the applicator roll and the pattern of the depressions. When the particulate material is decorative, the roll is provided with a decorative image that will be repeated on the substrate.

Figure 6:
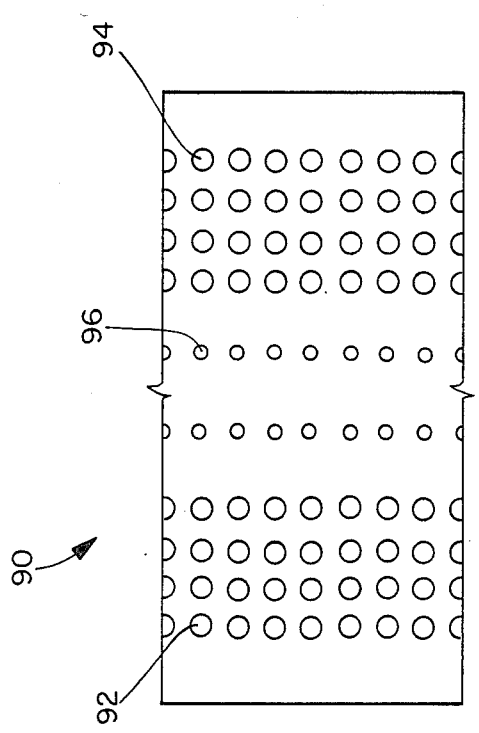
FIG. 6 is a view of an applicator roll in accordance with the invention.
Figure 7:
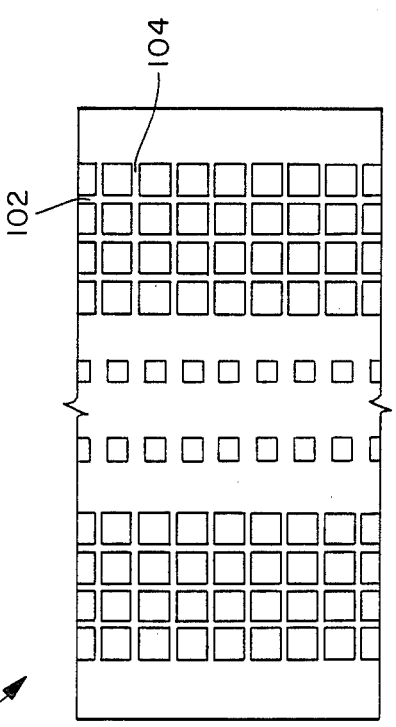
FIG. 7 is a view of the adhesive applicator intended for use with the applicator roll of FIG. 6.

FIG. 6 represents a roll 90 that has a series of large depressions 92 and 94 that are in bands toward the periphery of the roll. The center portion of the roll has a series of smaller depressions 96. Illustrated in FIG. 7 is the adhesive application roll 100 that is constructed so as to match with the discrete areas of particulate matter laid down by the roll 90. The adhesive application roll 100 has a series of lands 102 running in the direction of rotation and another series 104 running perpendicular to the direction of the rotation. These lands are carefully structured to provide adhesive to a covering web such that when combined with the receiving substrate the adhesive areas will surround the particulate matter deposited by the bands 92, 94, and 96 of roll 90. If rolls 90 and 100 are utilized to deposit superabsorbent, a pad would be formed that had high absorbency areas on its outer edges, with areas of less absorbency in the center section. Such a structure may be desirable for superabsorbents if it was desired that liquids would pass along the center portion of the pad and be absorbed primarily in the edges. Such a structure may be desirable if the center section was desired to be thinner or is subjected to higher pressure in use. Conversely, these may be reasons to design a structure with greater amounts of superabsorbents at the edges in order to allow good transfer of liquids along the center portion of the structure.

Figure 8:
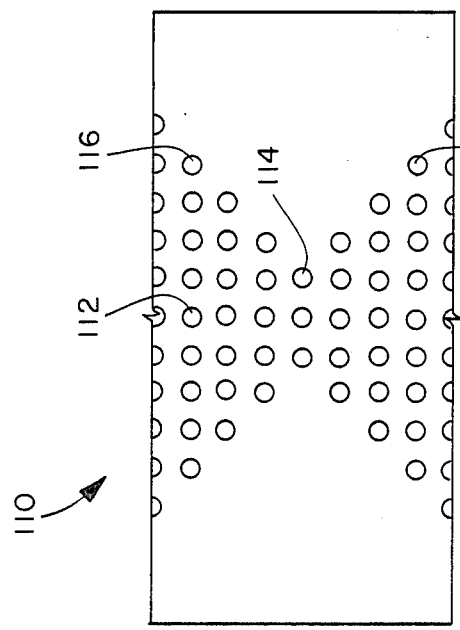
FIG. 8 is a view of a patterned particle applicator roll.
Figure 9:
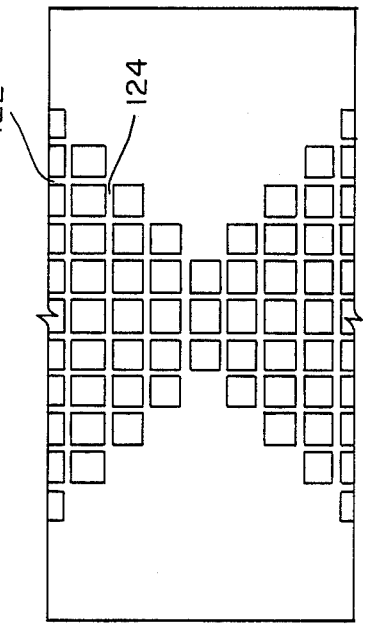
FIG. 9 is an adhesive applicator roll that is intended for use with the applicator roll of FIG. 8.

An alternative construction representative of advantages possible with the invention is illustrated by the particulate applicator roll 110 of FIG. 8 and the adhesive applicator roll 120 of FIG. 9. The applicator roll in FIG. 8 has a series of depressions 112 that form a pattern. The pattern is illustrated and is particularly suitable for forming an absorbent garment such as a diaper or incontinent garment. The pattern has a narrow portion 114 that would be the garment crotch and wider areas 116 and 118. The size of the roll is adjusted to create the patterns for two garments on one revolution. Illustrated in FIG. 9 roll 120 has the corresponding pattern of lands and valleys for adhesive application. These land areas 122 running parallel with the direction of rotation of the roll and land area 124 running perpendicular to that direction are constructed so as to surround the discrete areas of particulate matter placed by the indentations 112 in roll 110. While the patterns of rolls 90 and 110 are illustrated with reference to the application of superabsorbent, it is, of course, within the invention to apply other particulate materials such as colored polymers for decorative purposes.

Figure 10:
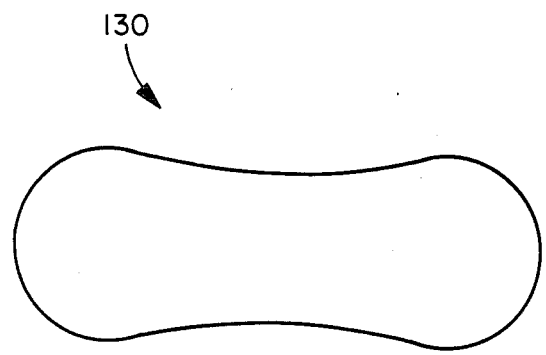
FIG. 10 is a plan view of a feminine pad.
Figure 11:
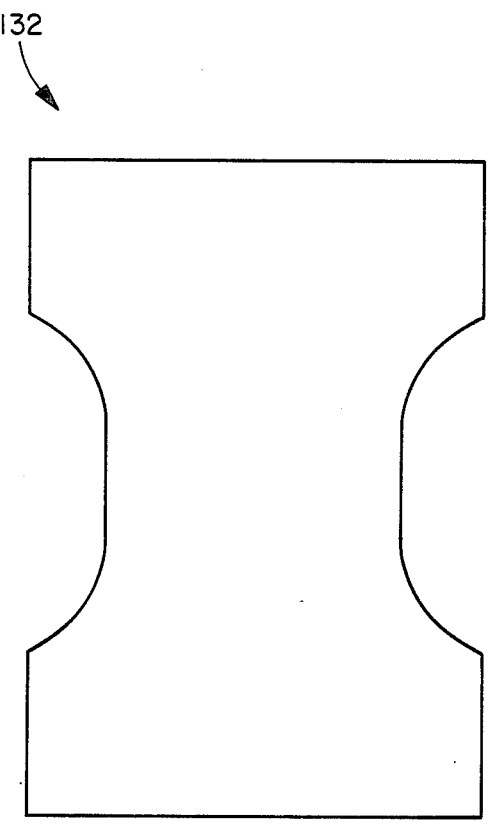
FIG. 11 is a plan view of a diaper.

FIGS. 10 and 11 illustrate in plan view products suitable for formation from pads formed with the superabsorbent application of the invention. FIG. 10 illustrates a feminine hygiene pad 130 that would benefit from the superabsorbent, particularly a zoned superabsorbent possible with the invention.

FIG. 11 represents a diaper 132 that could be formed utilizing the superabsorbent application of the invention. It particularly would benefit from superabsorbent applications such as illustrated in FIGS. 8 and 9 with a zoned superabsorbency following the crotch region of the diaper. The techniques of forming absorbent pads and garments, such as diapers and feminine pads, from continuous webs are well known and do not form a portion of this invention. The particular patterns of decorative or ornamental materials could be formed for eventual formation into a variety of products by conventional means.

Figure 12:
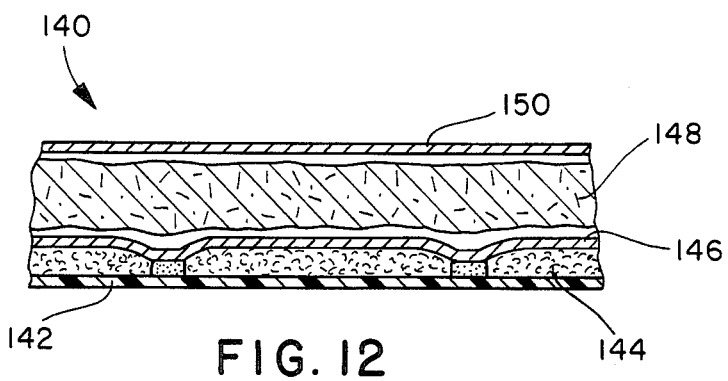
FIG. 12 is a fragmentary cross section of an absorbent pad in accordance with the invention.

FIG. 12 illustrates a cross section of a typical absorbent pad such as utilized in a diaper, containing the discrete areas of superabsorbent of the invention. As illustrated in FIG. 12, the absorbent pad 140 is comprised of an impervious-backed member 142, discrete areas of superabsorbent 144, a permeable member 146 overlaying the areas of superabsorbent 144. In the middle portion of the pad is an absorbent 148 such as fluff or coform material that has the ability to rapidly absorb liquids. The combination of fluff or coform with superabsorbent below it in the pad 140 allows the rapid absorption of liquids into the bulk absorbent layer 148 with this liquid then taken up by the superabsorbent 144 in the discrete piles. Overlaying on the body-side of the pad is a permeable liner 150, typically formed of material such as a permeable spunbonded polypropylene. Such a general absorbent structure is suitable for a variety of absorbent members such as bandages, incontinent garments, diapers, feminine pads, bed pads and other members adapted for absorption of bodily secretions. The impermeable backing member may be a film of polymer such as polypropylene or polyethylene or it may be a foam web or nonwoven fabric laminated to an impermeable web. This structure is also suitable for absorption of liquids other than in bodily secretions such as oil spills, floor pads or for use in multipurpose wipes.

Figure 13:
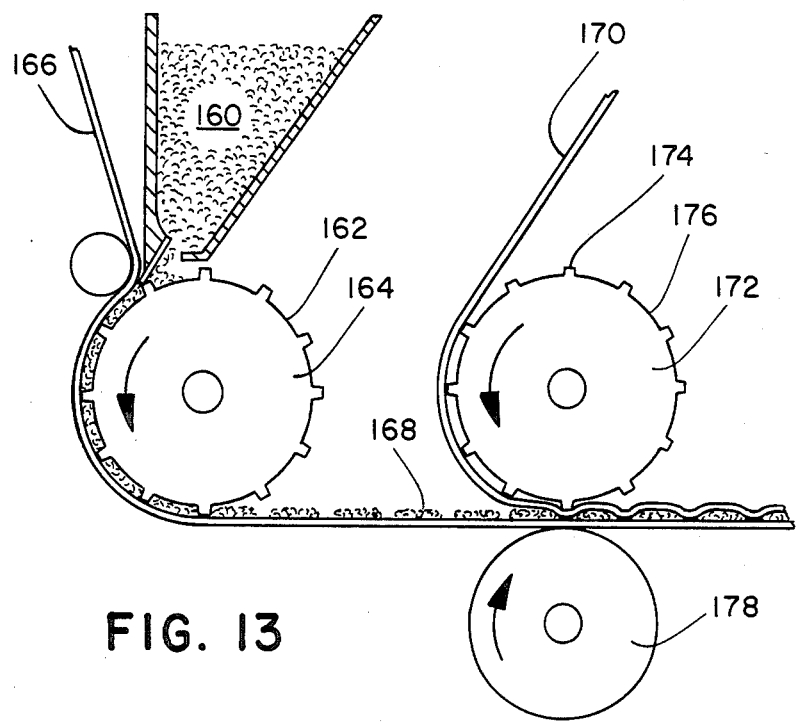
FIG. 13 is a schematic of alternate apparatus of the invention.

FIG. 13 illustrates an alternative apparatus in accordance with the invention. The apparatus of FIG. 13 comprises a source of particulate material 160 that is adapted to dispense particulate matter into the depressions 162 of roll 164. The material dispensed into roll 164 is transferred to the receiving sheet 166 to form individual discrete piles of material 168. The sheet 166 bearing the discrete piles of material 168 is formed of a material that is heat-sealable such as a polymer sheet. This receiving sheet or web bearing the particulate matter 168 is passed beneath the covering web 170. The cover web 170 is also formed from a heat-fusible material such as polypropylene. It is noted that at least one of the heat-fusible materials should be porous, either by perforations or by formation as a spunbonded material that is permeable. Roll 172 is heated and is composed of a surface having lands 174 and valleys 176. The receiving and covering sheets bearing the particulate matter 168 pass between heater rolls 172 and backup roll 178. Backup roll 178 may also be heated. The lands 174 of roll 172 are arranged to surround each discrete area of particulate matter 168. As the heated rolls press the fusable web 170 and 166, the areas at the lands are fused together, forming fused areas surrounding pocket areas containing the particulate matter. After the composite bearing the discrete elements of particulate matter is formed, it may be utilized in any of the manners set forth above such as in absorbent materials if the particulate matter is an absorbent.

Figure 14:
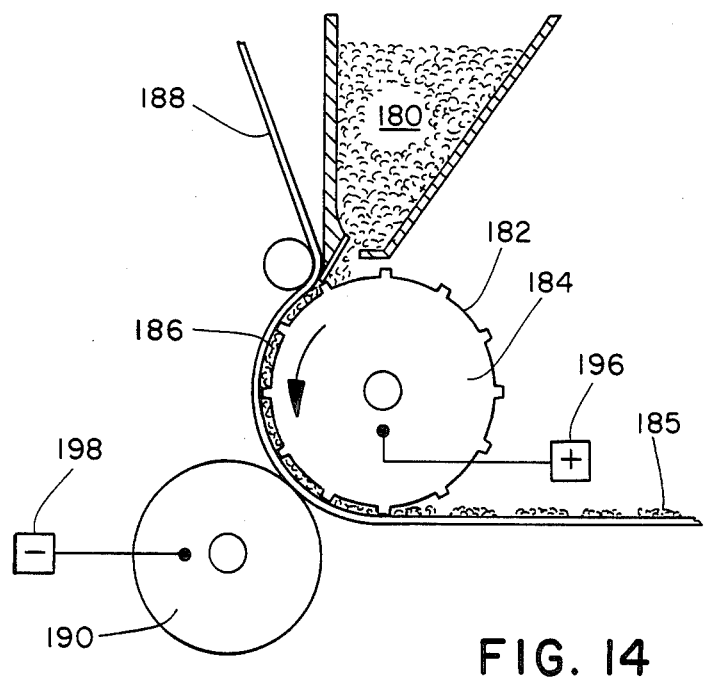
FIG. 14 is a schematic of an alternate particulate applicator in accordance with the invention.

FIG. 14 is another alternative illustrating an alternative method of transfer of the particulate material. As illustrated in FIG. 14, the hopper device containing particulate matter 180 feeds particulate matter into the depressions 182 of roll 184. The particulate matter 186 is transferred to the web 188. The transfer is aided by the use of negative charge on a transfer roll 190. The depositing roll 184 carries a positive charge such that there is an attraction from the depressions 182 onto the receiving web 188 in the area where transfer takes place between rolls 190 and 184. Roll 196 represents a means of positive charge, while 198 represents a means of negative charge. The receiving sheet 188 bearing the particulate material 185 may be combined either by adhesives or fusing to form articles as before described in the description of FIGS. 1 and 13.

By superabsorbent as used herein is meant an inorganic or organic hydrogel compound capable of absorbing aqueous fluids and retaining them under moderate pressures. For good results, the hydrogels are preferably at least somewhat water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug. 26, 1975.

Particularly preferred polymers for use herein are hydrolyzed acrylonitrile grafted starch, acrylic acid grafted starch, polyacrylates, and isobutylene maleic anhydride copolymers, or mixtures thereof. Processes for preparing hydrogels are disclosed in U.S. Pat. No. 4,076,663, issued Feb. 28, 1978 to Fusayoshi Masuda et al.; in U.S. Pat. No. 4,286,082, issued Aug. 25, 1981 to Tsuno Tsubakimoto et al.; and further in U.S. Pat. Nos. 3,734,876, 3,661,815, 3,670,731, 3,664,343, 3,783,871, Belgian Pat. No. 785,858.

As used herein "Particles" include particles of any shape, e.g. spherical or semispherical, cubic, rod-like, polyhedral, etc.; but also shapes having a large greatest dimension/smallest dimension ratio, like needles, flakes and fibers, are contemplated for use herein. By "particle size" as used herein is meant the weight average of the smallest dimension of the individual particles. Conglomerates of hydrogel particles may be used, provided the weight average size of such conglomerates is within the limits set forth hereinbelow.

Although the invention has been described with primary reference to superabsorbent materials, it is also within the invention to apply other particulate materials to the webs. As discussed above, the use of decorative colorants would be one possibility. Further, the formation of bandages or pads that would contain antiodorants in discrete areas is also possible. A further use would be the placement of wetness indicators that would be dissolved from the surface of the web by liquids when the pad was wet. Particulate materials having water-soluble wound treatment medicinal character also could be placed into a pad such that when the pad is wet either prior to application or by body fluids that treatment material would be replaced for germicidal or bactericidal action.

It is noted that while the descriptions have illustrated apparatus in processes wherein the particulate matter is transferred to the impermeable sheet 188, it is also possible that the particulate matter could be formed between two permeable members that could be inserted as a separate sheet into a variety of absorbent structures. Further, the superabsorbent could be placed between two impermeable sheets that are storage stable but may be needled prior to use to form permeable absorbent inserts.

The invention also may be utilized to form medical or edible materials utilizing edible papers as the cover sheets. For instance a powder for forming drink instant ice tea or coffee may be applied by the invention particulate applicator and sealed between edible sheets of paper. The receiving and covering sheets of edible paper may be sealed by wetting which acts as a glue or by utilizing edible glues of cellulose or animal base. Edible paper such as disclosed in the Package Engineering article of April 1971, pages 58-61 titled "Edible, Water-soluble Films Break the Machinability Barrier" by George A. Politis and James J. McCabe may be utilized. The edible papers discussed therein are formed of an amylose starch film. Another edible paper is that disclosed in U.S. Pat. No. 3,936,347—Nomura. The paper of Nomura is formed from pullulan that is a linear compound secreted by a particular micro-organism pullularia pullulans.

The advantage of packaging of particulate food products or medical products in the paper that is edible is that the amount of the amount to be mixed with the liquid may be readily controlled by cutting or tearing off a desired quantity. Further, there is no waste in that both the container and the food material are ingested. This would be particularly desirable for uses such as in camping or backpacking where weight and not generating garbage to be disposed of is important. Particulate food products, such as powdered drinks, are well suited for handling by the applicator roll of the invention containing depressions. Further, the invention method of dividing particulate matter into separate discrete areas by sealing around them is well suited for formation of easily regulated amounts of medicine, drink or food quantity as the amount of medicine, food or drink may be easily regulated by tearing off or cutting off the desired amount. For instance, by merely tearing or cutting off the right amount a glass or pitcher of powdered drink could be provided. The medicine doses for different age or weight persons also may be regulated in the same way. Sealing means for the separate compartments generally is not difficult with the edible papers as they may be sealed by edible animal glues or starch glues or by applying a small amount of water to the paper that will dissolve a small amount of the paper's surface and allow the adjacent papers to be joined where wetted. The paper may be later perforated in the sealed areas to aid in tearing the desired portions.

While the invention has been described with superabsorbent materials being held in a permeable laminate for absorption of liquids, the invention also could be utilized for holding other particulate material. For instance, it may be used for packaging food or medicine which would be released by cutting across the sealed areas. Further, the system could be utilized to place soluble colorant materials on the inside of the outer polymer covering of an incontinent garment. The colorant when wet would dissolve, causing a color change to indicate the garment was wet. These and other uses are intended to be included by the claims attached hereto.

I claim:

1. A method of forming a composite structure comprising laying down discrete areas of particulate material on a receiving web, applying adhesive to areas of a covering web, bringing the two webs together, in such a manner that the adhesive areas do not overlay the discrete areas of said particulate material, thereby creating discrete pockets of particulate material wherein said particulate material is laid down in discrete areas by being applied to depressions in a forming roll that is then rotated into contact with the receiving web and wherein said discrete areas of particulate material are in a pattern having a greater number of said depressions in the areas of the roll where more particulate material is desired and wherein said laying down on said receiving web is by electrical attraction.

2. The method of claim 1 wherein said particulate material comprises a superabsorbent.

3. A method for forming a composite structure comprising laying down discrete areas of particulate material on a receiving web, applying adhesive to areas of a covering web, bringing the two webs together, in such a manner that the adhesive areas do not overlay the discrete areas of said particulate material, thereby creating discrete pockets of particulate material wherein said particulate material is laid down in discrete areas by being applied to the depressions in a forming roll that is then rotated into contact with the receiving web and wherein said discrete areas of particulate material are in a pattern on said roll having larger depressions in the areas where more particulate material is desired and wherein said laying down is by electrical attraction.

4. The method of claim 3 wherein said particulate material comprises a food material.

5. The method of claim 3 wherein said covering web and said receiving web comprise edible papers.

6. The method of claim 3 wherein said particulate matter is laid down on said forming roll in a pattern of discrete areas having a greater number of said depressions in the areas where more particulate material is desired and then said particulate material is layed down onto said receiving web from said forming roll.

7. The method of claim 3 wherein said particulate material comprises superabsorbent.

8. The method of claim 3 wherein said particulate material is laid down in a pattern of discrete areas having a greater number of said depressions in the areas where more particulate material is desired.

9. The method of claim 3 wherein said laying down of particulate material is by gravity from a roll having indentations.

10. The method of claim 3 wherein at least one of said webs comprises tissue.

11. The method of claim 3 wherein said discrete areas of particulate material contain differing amounts of particles.

12. The method of claim 3 wherein said receiving web is a polymer sheet.

13. The method of claim 3 wherein said covering web is a permeable web.

14. The method of claim 3 wherein said particulate material comprises a food material and said receiving web and covering web comprise edible papers.

* * * * *